United States Patent [19]
Ortlieb et al.

[11] Patent Number: 4,759,221
[45] Date of Patent: Jul. 26, 1988

[54] APPARATUS FOR THE DETERMINATION OF SURFACE CRACKS

[75] Inventors: Erhard Ortlieb, Kalchreuth; Peter Wahode, Neunkirchen, both of Fed. Rep. of Germany

[73] Assignee: Kraftwerk Union Aktiengesellschaft, Mülheim, Fed. Rep. of Germany

[21] Appl. No.: 27,484

[22] Filed: Mar. 17, 1987

Related U.S. Application Data

[63] Continuation-in-part of Ser. No. 827,322, Feb. 6, 1987, abandoned.

[30] Foreign Application Priority Data

Feb. 7, 1985 [DE] Fed. Rep. of Germany ....... 3504210

[51] Int. Cl.[4] ............................................. G01N 29/00
[52] U.S. Cl. ......................................... 73/627; 73/602
[58] Field of Search ................. 73/602, 627, 620, 648, 73/659, 657, 622, 629, 637, 638

[56] References Cited

U.S. PATENT DOCUMENTS

| 4,052,889 | 10/1977 | Mucciardi et al. | 73/629 |
| 4,274,288 | 6/1981 | Tittmann et al. | 73/602 |
| 4,428,235 | 1/1984 | Sugiyama | 73/602 |
| 4,428,237 | 1/1984 | Zeger et al. | 73/602 |
| 4,545,250 | 10/1985 | Miwa | 73/602 |

Primary Examiner—Jerry W. Myracle
Assistant Examiner—Louis M. Arana
Attorney, Agent, or Firm—Herbert L. Lerner; Laurence A. Greenberg

[57] ABSTRACT

An apparatus for determining the depth of cracks in the surfaces of workpieces includes an ultrasonic transducer for sending ultrasonic signals to and receiving ultrasonic signals from the workpiece, an analyzer connected to the ultrasonic transducer for forming a frequency spectrum from the ultrasonic signals, an evaluating unit connected to the analyzer for determining an effective band width correlated with the depth of the cracks in the workpiece as the quotient of the integral of the frequency spectrum and the ordinate value of the center of concentration of the integrated surface of the frequency spectrum, and an indicator connected to the evaluating unit for indicating the depth of the cracks.

3 Claims, 1 Drawing Sheet

U.S. Patent
Jul. 26, 1988
4,759,221
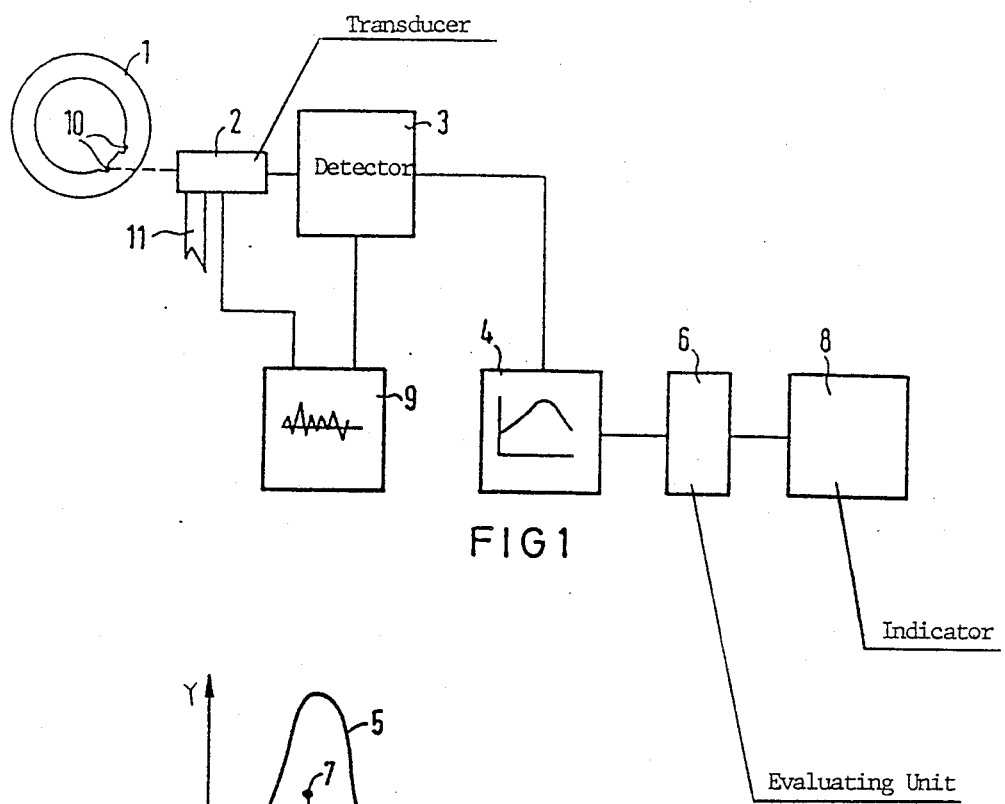
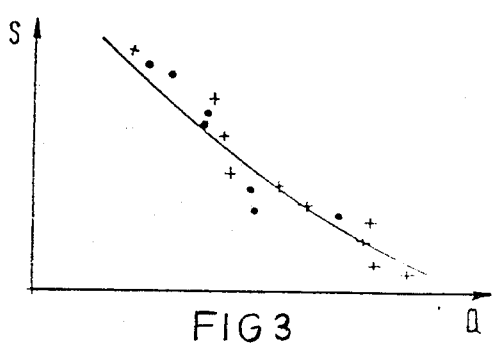

APPARATUS FOR THE DETERMINATION OF SURFACE CRACKS

This application is a continuation-in-part of Ser. No. 827,322 now abandoned.

The invention relates to an apparatus for the determination of the depth of cracks in the surfaces of workpieces, including an ultrasonic transducer.

Such an apparatus is known from the publication by Krautkrämer entitled: Werkstoffprüfung mit Ultraschall (Material Testing with Ultrasonics) Chapters 3.2 and 1.10. In this connection, ultrasonic waves are produced by an ultrasonic transducer and the echoes reflected by a crack in a workpiece are recorded. The reflected signal is received by the ultrasonic transducer and then evaluated. The magnitude of the echo signal which is measured then gives an indication of the crack depth.

The apparatus includes a detector for the reflected signal and an evaluation unit which calculates the amplitude of the signal as a measure of the depth of the crack.

With such an apparatus, the recorded signal amplitude is not correlated with the depth of the crack, particularly for relatively small cracks. There is indeed a correlation with test grooves which have been given a regular, generally V-shaped profile, but this is not repeatable with respect to the signal thereof, because of the irregular shape of natural cracks.

In addition, the testing reliability of the apparatus is limited by the wavelength of the ultrasonic waves doing the detecting. The identification of cracks with a depth which is essentially less than the ultrasonic wavelength becomes less reliable as the ratio of the crack depth to the wavelength decreases.

It is accordingly an object of the invention to provide an apparatus for the determination of surface cracks in workpieces by means of ultrasonics, which overcomes the hereinafore-mentioned disadvantages of the heretofore-known devices of this general type, and which guarantees a basic correlation between a measured signal and the depth of a crack independently of the shape of the crack.

In this way, the depth of the crack is to be determined from the reflected signal for any crack. Moreover, small cracks themselves are to be identified using the apparatus.

With the foregoing and other objects in view there is provided, in accordance with the invention, an apparatus for determining the depth of cracks in the surfaces of workpieces, comprising an ultrasonic transducer for sending ultrasonic signals to and receiving ultrasonic signals from the workpiece, an analyzer connected to the ultrasonic transducer for forming a frequency spectrum from the ultrasonic signals, an evaluating unit connected to the analyzer for determining an effective band width correlated with and being a measure of the depth of cracks in the workpiece as the quotient of the integral of the frequency spectrum and the ordinate value of the center of concentration of the integrated surface of the frequency spectrum, and an indicator connected to the evaluating unit for indicating the depth of the cracks.

The correlation is obtained by placing the known depth of artificially produced test grooves in a relationship with the measured effective band width. The testing reliability is improved for small cracks by the choice of a higher ultrasonic frequency.

The advantage obtained with the apparatus according to the invention is that the effective band width which is obtained from the signal that is received instead of an amplitude, is independent of the profile shape of the crack. A correlation determined from test grooves with V-profiles is therefore repeatable with natural cracks having irregular shapes.

In accordance with another feature of the invention, the workpiece is a cladding tube having two test grooves of given depth formed therein, and including a manipulator on which the ultrasonic transducer is disposed for shifting the transducer and measuring effective band widths deviating relatively widely from one another for the test grooves. This is done in order to determine a correlation with respect to test grooves.

The ultrasonic transducer is first shifted with the manipulator for two different test grooves of given depth in a cladding tube until two effective band widths are measured. The grooves are selected such that they have effective band width values that are as far from one another as possible. Next, in order to obtain still better accuracy of the measurements, the effective band widths of additional test grooves, having known depths, can be determined. After subsequent calibration, the depth can be determined according to the invention for differently shaped cracks in a cladding tube with great precision and can be supplied to an indicator. Cladding tubes for reactor fuel rods, for example, can therefore be checked reliably.

Other features which are considered as characteristic for the invention are set forth in the appended claims.

Although the invention is illustrated and described herein as embodied in an apparatus for the determination of surface cracks, it is nevertheless not intended to be limited to the details shown, since various modifications and structural changes may be made therein without departing from the spirit of the invention and within the scope and equivalents of the claims.

The construction and method of operation of the invention, however, together with additional objects and advantages thereof will be best understood from the following description of specific embodiments when read in connection with the accompaying drawings, in which:

FIG. 1 is a block circuit diagram of an apparatus for the determination of the depth of surface cracks in cladding tubes, shown diagrammatically in the figure;

FIG. 2 is a graph of the frequency spectrum of an ultrasonic signal reflected at the inner surface of the cladding tube and FIG. 3 is a graph of the functional dependence of the depth of a crack on the effective band width.

Referring now to the figures of the drawings in detail and first, particularly, to FIG. 1 thereof, it is seen that a cladding tube 1 for fuel rods of a nuclear reactor can have cracks 10 on the surface thereof. An ultrasonic transducer 2 which may be shifted on a manipulator 11 detects these cracks 10 by sending ultrasonic signals and receiving echoes reflected at the cracks 10 in the inner surface of the cladding tube 1. The output signal of the ultrasonic transducer 2 is supplied to a detector 3 which is adjusted in such a way that it reliably detects an ultrasonic impulse coming from a crack 10 in the cladding tube 1. An oscilloscope 9 is connected to the ultrasonic transducer 2 and to the detector 3 for monitoring the signals. A frequency spectrum 5 is produced for the detected impulse by Fourier analysis in an analyzer 4, as seen in FIG. 2.

For further evaluation of the frequency spectrum 5, the output of the analyzer 4 according to FIG. 1 is connected to an evaluating unit 6. The area below the frequency spectrum 5 is determined by integration in the evaluating unit 6. In addition, the coordinates of the center of gravity or center of concentration 7 of this area and, as the effective band width Q, the quotient of the area under the frequency spectrum 5 and the ordinate value Y of the center of concentration, are determined. This effective band width Q is correlated with the depth S of the cracks 10 in the cladding tube 1.

The shape of the cracks 10 is not worked out at the depth indicator. According to FIG. 3, pairs of values for the crack depth S and the effective band width Q both for test grooves with V-profiles (indicated by crosses) as well as for natural cracks (indicated by dots), lie with sufficient accuracy on a curve.

The relationship obtained by calibration with V-shaped test grooves is stored in the evaluating unit 6. With each measurement of irregular grooves in the cladding tube 1, the depth S of the crack can be determined in the evaluating unit 6 from the frequency spectrum 5 of the reflected pulses.

The evaluating unit 6 is connected to an indicator or recording unit 8 which records the depth S of the cracks 10 in the wall of the cladding tube 1, for example in micrometers.

We claim:

1. Apparatus for determining the depth of cracks in the surfaces of workpieces, comprising an ultrasonic transducer for sending ultrasonic signals to and receiving ultrasonic signals from the workpieces, an analyzer connected to said ultrasonic transducer for forming a frequency spectrum from the ultrasonic signals, an evaluating unit connected to said analyzer for determining, as a measure of the depth of the cracks, an effective band width determined as the quotient of the area below said frequency spectrum and the ordinate value of the center of gravity of said area of said frequency spectrum, and an indicator connected to said evaluating unit for indicating the depth of the cracks.

2. Apparatus according to claim 1, including a slidable manipulator on which said ultrasonic transducer is mounted.

3. Apparatus according to claim 1, wherein the workpiece is a cladding tube having two test grooves of given depth formed therein, and including a manipulator on which said ultrasonic transducer is disposed for shifting said transducer and measuring effective band widths deviating relatively widely from one another for the test grooves.

* * * * *